United States Patent [19]

Owen

[11] Patent Number: 4,696,903
[45] Date of Patent: Sep. 29, 1987

[54] METHOD AND APPARATUS FOR EXAMINING EARTH FORMATIONS

[75] Inventor: Murl Owen, Chanute, Kans.

[73] Assignee: Lalos & Keegan, Washington, D.C.

[21] Appl. No.: 451,970

[22] Filed: Dec. 21, 1982

[51] Int. Cl.$^4$ .................. G01N 31/22; G01N 21/01
[52] U.S. Cl. ................................. 436/28; 250/256; 436/139
[58] Field of Search .................. 73/151, 38; 116/206, 116/276, DIG. 41; 166/250, 253; 175/44, 46; 250/256; 354/63, 62; 356/70; 358/98, 100; 422/68, 69; 436/25, 28–31, 139

[56] References Cited

U.S. PATENT DOCUMENTS

| 2,206,922 | 7/1940 | Smith | 436/29 X |
| 2,849,530 | 8/1958 | Fleet | 358/100 |
| 2,912,495 | 11/1959 | Moon et al. | 358/100 |
| 4,204,528 | 5/1980 | Termanini | 354/62 X |
| 4,238,158 | 12/1980 | Sington | 250/256 X |

FOREIGN PATENT DOCUMENTS

| 529438 | 4/1974 | U.S.S.R. | 166/250 |
| 791956 | 6/1978 | U.S.S.R. | 250/256 |

Primary Examiner—Hiram H. Bernstein
Assistant Examiner—Michael S. Gzylowski
Attorney, Agent, or Firm—Lalos & Keegan

[57] ABSTRACT

A method and apparatus are described for logging an open hole well, or the like, for the purpose of determining the presence of a given constituent in the various substrata and for providing means and method for determining the degree of presence of the constituent in a given formation where it has been located. A probe capable of being lowered into a bore hole includes a color video camera, a particular form of light source, apparatus for carrying and issuing a spray of cleaning substance and apparatus for carrying and issuing a chemical which facilitates the analysis of the degree of presence of the constituent. The probe is lowered to the bottom of the bore hole and then raised to a desired level. A cleaning jet sprays the surface to be inspected. The cleaned surface is then illustrated with light having a frequency in a predetermined frequency range and the reflected light is directed to the camera. The video signal is conducted to the surface where it is displayed. Examination of the color content of the video display allows for determination of the presence or absence of the constituent in question. Should it be determined that this constituent is present the formation undergoing examination is sprayed with a colorant which, when illuminated, provides a reflected light, the intensity of the color produced by the reflected light is in correspondence with the degree of presence of the constituent in the formation being examined.

6 Claims, 4 Drawing Figures

METHOD AND APPARATUS FOR EXAMINING EARTH FORMATIONS

BACKGROUND OF THE INVENTION

This invention relates to well logging and, more particularly, to the means and method for providing a direct visual indication of the presence of a predetermined constituent of an earth formation.

Various techniques and apparatus are now used for the purpose of well logging to study the properties of subsurface formations to determine the presence or absence of given naturally occurring substances, such as oil. The principal techniques presently being used either involve the taking of a core sample from the bore hole and subsequently chemically analyzing it, or measuring the radioactive properties of the subsurface formations. In either case the measurement techniques are complex, and the means by which results are actually determined are similarly complex. Moreover, the results of any such measurement are not produced immediately, and a relatively long period of time is required before a determination can be made regarding the content of the subsurface formations being examined.

Using core sample techniques it is necessary to physically remove a portion of the subsurface formation being examined to what is substantially a laboratory environment to permit a chemical analysis. There the core sample is chemically analyzed to determine its constituents and, particularly, to determine the degree of presence of the substance being sought, such as oil. Obviously, this technique is cumbersome, and presently available methods of chemical analysis of such core samples require significant periods of time before completion. In many circumstances, particularly in an oil drilling environment, such losses of time are economically disadvantageous.

The other major technique for well logging involves the use of means for studying the radioactive properties of the subsurface formations in question. This technique could involve the measurement of natural radioactive properties, or it could involve measurements wherein the radioactivity is artificially induced. The means by which this radioactivity is measured are complex, expensive and often unreliable in the harsh environment in which they must be used. For example, in the case where gamma radiation is being measured, crystals must be used which respond to the gamma radiation to thereby produce light energy which is subsequently converted to electrical energy having a complex wave form. It is then necessary to rigorously analyze the wave form content of the aforementioned electrical signal, and this analysis often requires the aid of a computer. It is only after this complex mathematical analysis of the electrical wave form generated as described above is completed can there be made a determination as to the presence or absence of the substance being sought in the earth formation being analyzed. Obviously, this technique requires complex and expensive apparatus and requires complex and time-consuming analysis procedures before a conclusion can be reached.

It is, therefore, an object of this invention to provide a means and method for examination of earth formations in, for example, a bore hole which will provide a direct and immediate indication of the presence or absence of a given substance in the formation.

It is another object of this invention to provide a means and method for the in situ examination of earth formations penetrated by a bore hole which utilizes relatively simple and inexpensive apparatus and requires no subsequent chemical or mathematical analysis.

An additional object of this invention is to provide a means and method for the examination of earth formations in a bore hole which are relatively simple to operate and which do not require the presence of highly skilled personnel to carry out the method nor to receive and understand the results.

SUMMARY OF THE INVENTION

The aforementioned and other objects are obtained in accordance with the principles of the invention through the use of a means and method for examining earth formations to determine the presence of a substance therein which includes illuminating the earth formation of interest with light of a given frequency. If it is petroleum hydrocarbons which are to be located, the earth formation is illuminated with light in the ultraviolet frequency range. The light reflected from the formation, so illuminated, is viewed for its color content. On the basis of the color content of this reflected light the presence or absence of the constituent of the earth formation of interest can be determined.

If it is desired to determine the degree of presence of the constituent in question, such as the ratio of oil to water in the formation being examined, the following additional technique is used. A colorant is used which will not dilute in water, and which has the capability of adhering to molecules of the substance, the presence of which in the earth formation is being analyzed. The amount of colorant which will remain and not be dissipated is in direct proportion to the number of molecules of the substance in question present. Thus, the greater the number of molecules of the substance, the more intense the presence of the colorant. This colorant then may be examined for its intensity by visual means, and this will bear a direct relation to the degree of presence of the substance in question.

BRIEF DESCRIPTION OF THE DRAWINGS

The principles of the invention will be more readily understood by reference to the description of a preferred embodiment of the means of the invention and a preferred mode of performance of the method of the invention described hereinbelow in conjunction with the drawings which are briefly described as follows.

DETAILED DESCRIPTION OF THE DRAWINGS

Figure 1:
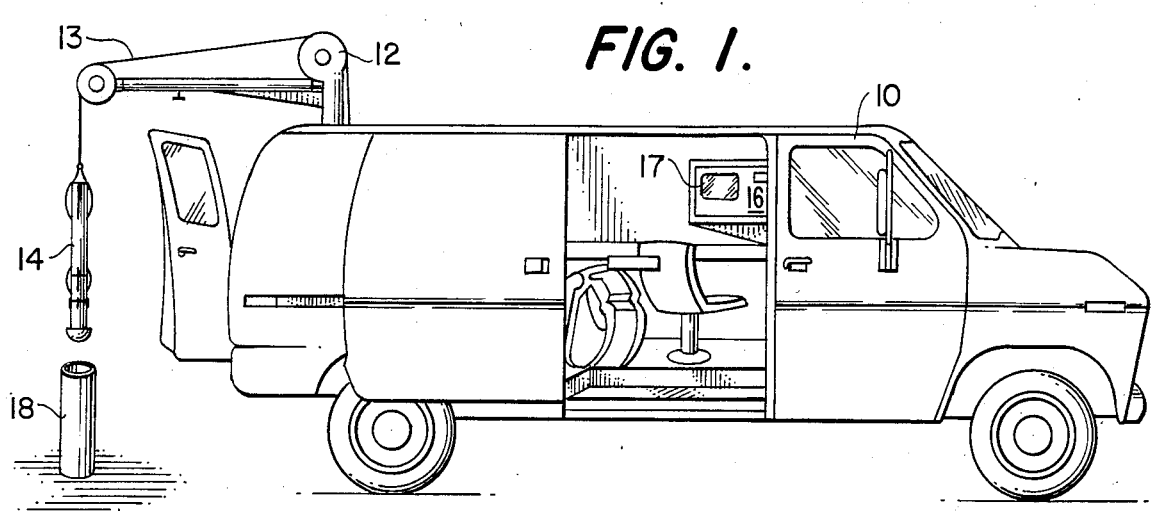
FIG. 1 is a perspective view of an assembly including a preferred embodiment of the invention as it may be used in an oil well logging environment.

In FIG. 1 is illustrated an assembly including the preferred embodiment of the invention. As is apparent, the means for carrying out the measurements in accordance with the invention may readily be carried in a van-type vehicle 10. Van 10 carries a winch mechanism 12 for operating cable 13 to support and raise and lower probe assembly 14. Cable 13 also carries in a coaxial fashion wires for connecting the probe assembly to a console 16 in van 10. A television signal communicated from probe 14 via cable 13 appears on video display 17 of console 16. A video tape recorder (not shown) may be provided for making a permanent record of the video display. At 18 is illustrated a casing for the bore hole within which probe 14 is to be lowered for examination of the earth formations therein.

Figure 2:
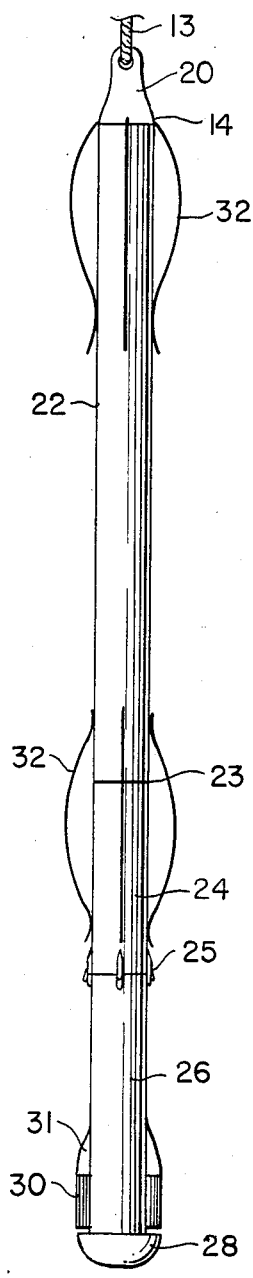
FIG. 2 is a side perspective view of a preferred embodiment of the probe assembly of the apparatus of the invention.

As illustrated in FIG. 2, probe 14 is connected to cable 13 by means of a control cable head 20. The probe is divided in this embodiment into three sections. The first of these sections 22 is mechanically connected to cable head 20 and carries a chemical tank assembly the uses for which will become more apparent from the description hereinbelow. Section 22 of probe 14 is connected at screw joint 23 to a section 24 which carries mechanical components, such as pumps for delivering the chemicals from section 22 in the manner to be described below.

A third section 26 is coupled to section 24 by means of cliplocks 25. A bottom bumper 28 is connected to the other end of probe section 26. This bottom bumper is of a material which will allow the probe to make physical contact with the bottom of a bore hole or the like and prevent the possibility of damage.

The means by which the visual examination of an earth formation is carried out, as well as the means for spraying an appropriate cleaning substance and colorant are contained in section 26 of the probe. In a manner to be more fully described hereinbelow the earth formation to be observed is isolated through extension of a bellows mechanism 30 to the sides of the hole in the manner to be more fully described below. This bellows mechanism is carried in an outwardly tapered portion 31 of probe section 26, and surrounds openings 33a and 33b in portion 31 of the probe.

Arcuate members 32 are provided at various points around the periphery of the probe assembly in order to provide for centering of it within the bore hole and to prevent inadvertent contact with the sides of the bore hole and, perhaps, resulting damage.

Figure 3:
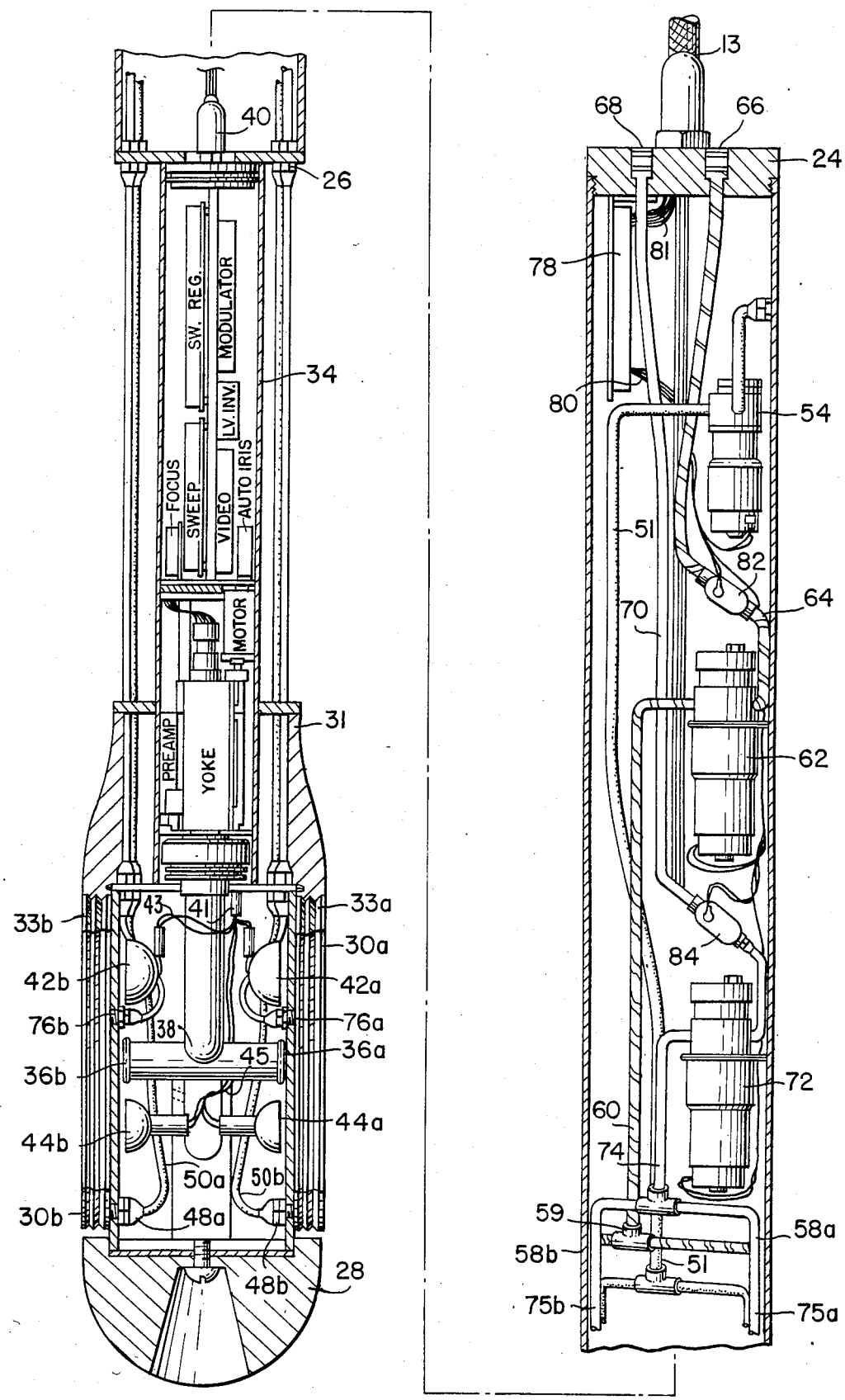
FIG. 3 is a side cross-sectional view of a portion of the FIG. 2 probe assembly and FIG. 4 is a partial cut-away view of FIG. 3.

FIG. 3 illustrates in cross-sectional view the working components of probe assembly 14 which are found in sections 24 and 26 thereof.

The probe assembly contains a coaxially constructed color video camera 34 which receives its visual images from lens 36a and 36b via right angle optical coupling 38. The lens 36a and 36b are mounted to receive light through openings 33a and 33b, respectively. Camera 34 is constructed in the conventional manner to provide the appropriate electronic signals resulting from the sensed light. These camera components and their operation, being conventional, will not be described further herein, but they are identified by appropriate legends in FIG. 3. In the preferred embodiment this camera is a Model 3800 color video camera manufactured by California Video Corporation. The electronic output from camera 34 appears at cable coupling 40 for communication through coaxial cable 13 to console 16 and video display 17.

For purposes of initial visual examination of the earth formation in question and for use in connection with this preferred embodiment for the determination of the presence of petroleum hydrocarbons, a pair of ultraviolet lights 42a and 42b are provided. These are, as well, mounted to emit light through openings 33a and 33b. The illustrated wire harness 41 carries wires 43 which connect with a power source for operating these lights. In addition, a pair of quartz lamps 44a and 44b are in this embodiment mounted below lens assembly 38 for purposes to be described, and wires 45 also carried in wire harness 42 provide the power for actuation and operation of these lights.

As briefly discussed hereinabove, bellows 30 is expanded during an examination operation to isolate the earth formation being examined. The bellows receives air under pressure through couplings 48a and 48b and branch conduits 50a and 50b which merge into a conduit 51 in probe section 24. Pumping pressure is supplied by an inflation pump 54 mounted as shown.

Figure 4:
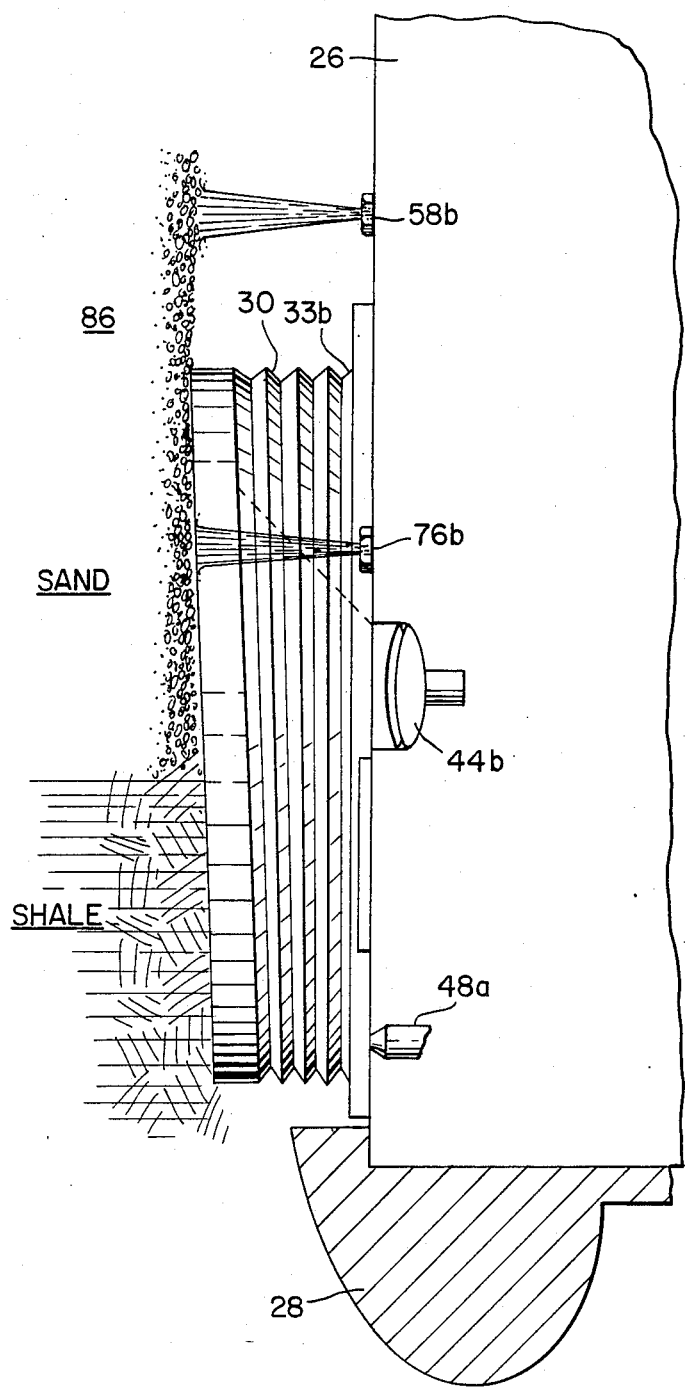

An initial phase of the earth formation examination technique of this invention involves a cleaning operation whereby the bore hole wall surface to be observed is sprayed with a suitable cleaning substance to remove foreign matter which would impede the visual observations to be made. For this purpose cleaning jets 58a and 58b are provided and are shown in FIG. 3 to be arranged substantially above what might be termed the operating end of the probe assembly or above openings 33a and 33b. As best shown in FIG. 4, the spraying action of these jets occurs somewhat above the portion of the bore hole wall to be viewed so that the spraying action and gravity will have the effect of cleaning the entirety of the viewed portion of the bore hole wall.

Jets 58a and 58b, via branch coupling 59, are in fluid communication with a pump 62 through conduit 60. Pump 62 receives the cleaning substance, which in this embodiment is salt water, via a conduit 64 which is connected to a first tank in section 22 of the probe assembly by means of fluid coupling 66.

A second aspect of the inventive technique involves the spraying of a colorant material onto the surface of the bore hole wall portion being viewed. This colorant material is stored in a second tank portion of probe assembly section 22 to which is connected a fluid coupling 68. This fluid coupling, via conduit 70, supplies the colorant to a pump 72 which in turn supplies the colorant material under pressure to conduit 74. The latter conduit is divided into branch lines 75a and 75b which are, respectively, in fluid communication with jets 76a and 76b. The colorant is described in greater detail hereinbelow.

Each of the pumps 54, 62 and 72 are operated from a power source 78 which, in this embodiment, is mounted near the upper end of probe section 24. It will be noted that the complex wiring harness exiting from power source 78 is connected to operate both the pumps and solenoids 82 and 84. The latter solenoids, respectively, control the flow of the respective fluid materials to pumps 62 and 72. The operation of power source 78 and solenoids 82 and 84 can be controlled in a conventional manner from the remote control station in van 10 via the wiring harness 81.

FIG. 4 illustrates the operation of the cleaning and colorant jets and their relation to the operation of the remainder of the system. This figure illustrates a cutaway section of probe section 26, or that portion of the probe section facing a bore hole wall section 86. When this section of the probe assembly is placed adjacent wall section 86, the initial operation which occurs is the expansion of the bellows followed by the spray cleaning operation from, in this case, jet 58b. The bellows 30 is inflated through jets 48a and 48b to isolate wall section 86, but a seal is not formed. Thus, the sprayed salt water impinges on the wall section after proceeding around the outer edge of the extended bellows.

Another phase of the operation following the extension of bellows 30 involves the spraying of a colorant material on wall portion 86, and this occurs through jets 76a and 76b.

The figure also illustrates the quartz light 44b which is actuated following the spraying of the colorant material to provide the visual indication discussed in greater detail hereinbelow.

In order to carry out a well logging operation in accordance with this invention it is contemplated that the probe assembly 14 will be lowered into bore hole 18 to the bottom thereof. Then, perhaps using drillers' logs, the probe will be raised to predetermined levels within the bore hole in order to carry out the observation techniques to be described in the following.

When the probe assembly 14 has been raised to a level having an earth formation to be examined, the bellows is expanded as described above. Subsequently, pump 62 is actuated, and solenoid valve 82 is opened to permit the flow of the cleaning chemical to jets 58a and 58b. The wall surface to be examined is then cleaned by means of the high pressure spray issuing from jets 58a and 58b and through the solvent action of the material as it flows down the wall surface through the force of gravity.

At this point, ultraviolet lights 44a and 44b are turned on, and the operation of the video camera 34 is initiated. These operations are, of course, initiated remotely in van 10 by conventional switching means. It has been found that when petroleum hydrocarbon molecules are illuminated with ultraviolet light a unique color characteristic will be produced in the reflected light. This reflected light is received through the lens 36a and 36b of camera 34 and by conventional electrical means is communicated to the viewing screen 17 in console 16. This provides a clear indication of the presence of oil in the earth formation being examined.

If it has been determined that oil is present in the earth formation being examined, it is then desirable to determine its degree of presence, e.g., the ratio of oil to water there present. For this purpose solenoid valve 84 is opened to allow the flow of colorant to pump 72, which is also actuated, so that a spray of colorant material issues from jets 76a and 76b. The colorant is selected to be a material which will not dilute in water and adheres to the molecules of the substance, the presence of which is being determined. In the case of operations where the presence of oil is to be determined, adherence to the hydrocarbon molecules is desired. Thus, the more of such hydrocarbon molecules which are present, the greater the degree of adherence of the colorant material. Further, a material may be selected which has a relatively neutral color but which has the effect of fluorescing when in adherence with hydrocarbon molecules. In this preferred embodiment the colorant is a lyophilic dye and preferably an aniline dye. The latter dye is formed, in a specific example, from a mixture of aniline black in an organic solvent, such as toluene or zylene. The proportion of these materials are chosen to form a mixture having a proper viscosity for spraying, while having sufficient aniline black to perform the dyeing function.

Quartz lights 44a and 44b are turned on during this spraying operation. The video camera 34 is again actuated and the color intensity of this scene may then be observed. By reason of the aforementioned adherence action of the colorant material, the greater the intensity of the known color, the greater the degree of presence of oil in the oil-water mixture. Therefore, by this means, the degree of presence of oil can be readily and immediately determined simply by visual inspection via viewing screen 17.

The entire operation described hereinabove may be repeated as many times as necessary at different depths in the bore hole as selected by conventional geological techniques.

While the invention described hereinabove has been described primarily from the standpoint of its use in locating petroleum deposits, it is contemplated that these principles may be applied to the location of other substances or materials. Further, it is contemplated that other selections of light frequencies may be used or that other specific chemical materials may be found to be useful to achieve the same ends.

It should, therefore, be remembered that although the invention has been described in connection with a specific application and a preferred embodiment, the description in the specification is considered to be only exemplary. Numerous changes in the construction of the apparatus described hereinabove and modifications in the selection of light frequencies and chemicals and the like may be resorted to without departing from the spirit and scope of the invention defined in the appended claims.

I claim:

1. A method for examining earth formations in a bore hole for determining the presence of petroleum hydrocarbon comprising the steps of:

illuminating a preselected formation with light having a frequency in the ultraviolet range, producing a visual display of the color characteristic of light selected from the illuminated formation, indicating the presence of petroleum hydrocarbons responsive to the presence of a predetermined color content of said visual display, applying a colorant to the formation being examined, said colorant having the characteristic that it adheres to petroleum hydrocarbon molecules, illuminating said preselected formation, producing a visual display of the color characteristic of light reflected from the illuminated formation, and indicating, additionally, the degree of presence of petroleum hydrocarbons responsive to a predetermined intensity of color produced by said colorant in said visual display.

2. A method of determining the ratio of petroleum hydrocarbon to water in a mixture thereof in an earth formation comprising the steps of:

applying a colorant to said earth formation, said colorant having the characteristics that it will not dilute in water and that it will adhere to petroleum hydrocarbon molecules, illuminating said earth formation to which said colorant is applied, producing a visual display of reflected light from said illuminated earth formation, and indicating from said visual display a predetermined petroleum to water ratio responsive to a predetermined intensity of the color produced by adherence of said colorant to said hydrocarbon molecules.

3. The method defined in claim 2 wherein said illuminating step comprises illuminating said earth formation with quartz light.

4. A method for examination of earth formations within a bore hole comprising the steps of:

illuminating a predetermined formation with light of a predetermined frequency, viewing the light reflected from the formation so illuminated, determining from the color content of the reflected light the presence or absence of a predetermined naturally occurring constituent of the earth formation, spraying the formation with a preselected colorant material, illuminating the formation, and determining from the intensity of color of the reflected light containing the color of the colorant material the degree of presence of said constituent.

5. The method defined in claim 4 wherein said spraying step occurs following the step of determining the presence or absence of said constituent from the color content of the reflected light.

6. The method defined in claim 4 wherein said viewing and illuminating steps are carried out at predetermined levels within said bore hole.

* * * * *